(12) United States Patent
Olson (10) Patent No.: US 12,011,549 B2
(45) Date of Patent: Jun. 18, 2024

(54) SHEATH VISUALIZATION

(71) Applicant: St. Jude Medical, Cardiology Division, Inc., St. Paul, MN (US)

(72) Inventor: Gregory K. Olson, Elk River, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 996 days.

(21) Appl. No.: 16/479,113

(22) PCT Filed: Jan. 19, 2018

(86) PCT No.: PCT/US2018/014430
§ 371 (c)(1),
(2) Date: Jul. 18, 2019

(87) PCT Pub. No.: WO2018/136741
PCT Pub. Date: Jul. 26, 2018

(65) Prior Publication Data
US 2019/0381274 A1    Dec. 19, 2019

Related U.S. Application Data

(60) Provisional application No. 62/447,967, filed on Jan. 19, 2017.

(51) Int. Cl.
*A61M 25/00* (2006.01)
*A61M 25/01* (2006.01)

(52) U.S. Cl.
CPC ...... *A61M 25/003* (2013.01); *A61M 25/0045* (2013.01); *A61M 25/0147* (2013.01);
(Continued)

(58) Field of Classification Search
CPC .. A61M 2025/0166; A61M 2205/0233; A61B 5/287; A61B 5/6852
See application file for complete search history.

(56) References Cited

U.S. PATENT DOCUMENTS 5,224,939 A   7/1993  Holman et al.
5,380,301 A   1/1995  Prichard et al.
(Continued)

FOREIGN PATENT DOCUMENTS

CN   101405052 A   4/2009
CN   101927053 B   1/2015
(Continued)

*Primary Examiner* — Jason E Flick
*Assistant Examiner* — Adam J. Cermak
(74) *Attorney, Agent, or Firm* — Kilpatrick Townsend & Stockton LLP (57) ABSTRACT

Medical devices and systems including electrical traces are provided. The medical device includes a sheath body (120) including an inner wall, an outer wall, and a central major lumen (20) extending through the sheath body (120) along a longitudinal axis. The central major lumen is defined by the inner wall. The medical device further includes at least one outer lumen (38) extending through said sheath body, wherein the at least one outer lumen (38) is disposed between the inner wall and the outer wall, at least one electrode (14) coupled to a distal portion of said sheath body (120), and at least one electrical trace (44). Each of the at least one electrodes (14) is coupled to at least one electrical trace (44), and the electrical trace (44) is disposed between the inner wall and the outer wall.

11 Claims, 6 Drawing Sheets

(52) U.S. Cl.
CPC .............. *A61M 2025/0166* (2013.01); *A61M 2205/0233* (2013.01)

(56) References Cited

U.S. PATENT DOCUMENTS

| | | | |
|---|---|---|---|
| 5,400,783 A | 3/1995 | Pomeranz et al. |
| 5,456,254 A | 10/1995 | Pietroski et al. |
| 5,626,136 A | 5/1997 | Webster, Jr. |
| 5,715,817 A | 2/1998 | Stevens-Wright et al. |
| 5,715,832 A | 2/1998 | Koblish et al. |
| 5,827,278 A | 10/1998 | Webster, Jr. |
| 5,876,373 A | 3/1999 | Giba et al. |
| 6,074,379 A | 6/2000 | Prichard |
| 6,078,830 A * | 6/2000 | Levin ................ A61B 18/1492 606/41 |
| 6,208,881 B1 * | 3/2001 | Champeau ......... A61B 18/1492 607/116 |
| 6,273,404 B1 | 8/2001 | Holman et al. |
| 6,491,681 B1 | 12/2002 | Kunis et al. |
| 6,554,794 B1 | 4/2003 | Mueller et al. |
| 7,004,937 B2 | 2/2006 | Lentz et al. |
| 7,214,220 B2 | 5/2007 | McGlinch et al. |
| 7,217,256 B2 | 5/2007 | Di Palma |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 * | 1/2012 | Harlev ................ A61B 5/287 600/509 |
| 8,137,321 B2 | 3/2012 | Argentine |
| 8,221,390 B2 | 7/2012 | Pal et al. |
| 8,273,016 B2 | 9/2012 | O'sullivan |
| 8,364,236 B2 * | 1/2013 | Burke ................ A61B 5/6858 600/509 |
| 8,376,990 B2 | 2/2013 | Ponzi et al. |
| 8,447,377 B2 | 5/2013 | Harlev et al. |
| 8,608,703 B2 | 12/2013 | Riles et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,755,861 B2 | 6/2014 | Harlev et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,486,280 B2 | 11/2016 | Koblish et al. |
| 9,486,282 B2 | 11/2016 | Solis |
| 9,539,413 B2 | 1/2017 | Ogle |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,694,159 B2 | 7/2017 | Schneider et al. |
| 9,694,161 B2 | 7/2017 | Selkee |
| 9,788,895 B2 | 10/2017 | Solis |
| 9,820,664 B2 | 11/2017 | Hoitink et al. |
| 9,844,645 B2 | 12/2017 | Pai et al. |
| 9,848,795 B2 | 12/2017 | Marecki et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,022 B2 | 11/2018 | Helgeson et al. |
| 10,143,394 B2 | 12/2018 | Solis |
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,702,677 B2 | 7/2020 | Okamura et al. |
| 10,737,060 B2 | 8/2020 | Gupta et al. |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,953,196 B2 | 3/2021 | Raab et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,141,568 B2 | 10/2021 | Hsueh et al. |
| 11,160,482 B2 | 11/2021 | Solis |
| 11,172,858 B2 | 11/2021 | Olson et al. |
| 11,272,886 B2 | 3/2022 | Harlev et al. |
| 2002/0165484 A1 | 11/2002 | Bowe et al. |
| 2005/0033136 A1 * | 2/2005 | Govari ................ A61B 5/287 606/41 |
| 2005/0060885 A1 * | 3/2005 | Johnson ............... A61N 1/0551 29/830 |
| 2007/0299424 A1 * | 12/2007 | Cumming ......... A61M 25/0012 604/527 |
| 2009/0143651 A1 * | 6/2009 | Kallback ............... A61B 5/287 600/374 |
| 2009/0171274 A1 * | 7/2009 | Harlev ................ A61B 5/287 604/95.04 |
| 2009/0240249 A1 * | 9/2009 | Chan ................ A61B 18/1492 606/41 |
| 2009/0247993 A1 | 10/2009 | Kirschenman et al. |
| 2009/0306653 A1 * | 12/2009 | Anderson .......... A61B 18/1492 606/41 |
| 2010/0010328 A1 * | 1/2010 | Nguyen ............... A61B 5/0215 600/364 |
| 2011/0118592 A1 * | 5/2011 | Sobe ................ A61B 17/3207 600/424 |
| 2011/0218602 A1 | 9/2011 | Kampa et al. |
| 2012/0010490 A1 * | 1/2012 | Kauphusman .......... A61B 5/287 600/373 |
| 2012/0130217 A1 * | 5/2012 | Kauphusman ....... A61B 5/6852 29/874 |
| 2012/0130218 A1 * | 5/2012 | Kauphusman ....... A61B 5/6852 600/585 |
| 2012/0143298 A1 * | 6/2012 | Just ................... A61B 18/1492 607/122 |
| 2012/0172717 A1 | 7/2012 | Gonda |

(56) References Cited

U.S. PATENT DOCUMENTS

| | | | |
|---|---|---|---|
| 2014/0100639 A1 | 4/2014 | Lee et al. | |
| 2014/0209372 A1* | 7/2014 | Sobe | A61B 5/062 |
| | | | 174/250 |
| 2014/0228838 A1* | 8/2014 | Kirschenman | G01L 5/00 |
| | | | 606/41 |
| 2014/0378803 A1* | 12/2014 | Geistert | A61B 5/287 |
| | | | 600/373 |
| 2015/0001191 A1 | 1/2015 | Lee et al. | |
| 2015/0082874 A1* | 3/2015 | Samproni | G01N 33/4915 |
| | | | 73/61.61 |
| 2015/0119911 A1 | 4/2015 | Mckenzie | |
| 2015/0182168 A1* | 7/2015 | Draper | A61L 29/06 |
| | | | 600/381 |
| 2015/0223729 A1* | 8/2015 | Balachandran | A61B 5/1076 |
| | | | 600/374 |
| 2015/0273184 A1* | 10/2015 | Scott | H01B 7/04 |
| | | | 29/842 |
| 2015/0305807 A1 | 10/2015 | Kelly et al. | |
| 2015/0366508 A1* | 12/2015 | Chou | A61B 5/287 |
| | | | 600/467 |
| 2016/0100768 A1* | 4/2016 | Someya | A61B 5/291 |
| | | | 29/829 |
| 2016/0113710 A1* | 4/2016 | Ogle | A61M 25/0012 |
| | | | 606/41 |
| 2016/0213423 A1 | 7/2016 | Kauphusman et al. | |
| 2016/0228678 A1* | 8/2016 | Cargill | C12Q 1/54 |
| 2016/0270732 A1* | 9/2016 | Källbäck | A61B 5/6852 |
| 2016/0278851 A1 | 9/2016 | Mannion et al. | |
| 2016/0331933 A1 | 11/2016 | Knutsen | |
| 2016/0338647 A1* | 11/2016 | Sterrett | A61B 5/6852 |
| 2017/0143414 A1* | 5/2017 | Sliwa | A61B 18/1492 |
| 2017/0164464 A1* | 6/2017 | Weinkam | G01K 7/16 |
| 2017/0164867 A1* | 6/2017 | Kassab | A61B 5/7225 |
| 2017/0319269 A1 | 11/2017 | Oliverius et al. | |
| 2017/0367756 A1 | 12/2017 | Sliwa et al. | |
| 2018/0042667 A1 | 2/2018 | Pappone et al. | |
| 2018/0085064 A1 | 3/2018 | Auerbach et al. | |
| 2018/0093078 A1* | 4/2018 | Patil | A61B 5/027 |
| 2018/0160936 A1* | 6/2018 | Govari | A61B 18/1492 |
| 2018/0161093 A1 | 6/2018 | Basu et al. | |
| 2018/0263688 A1* | 9/2018 | Barrish | A61B 18/1492 |
| 2019/0025040 A1* | 1/2019 | Andreason | A61B 5/062 |
| 2019/0192826 A1 | 6/2019 | Wada | |
| 2019/0223758 A1* | 7/2019 | Just | A61B 5/6852 |
| 2020/0138378 A1 | 5/2020 | de la Rama et al. | |
| 2020/0253496 A1 | 8/2020 | Deno et al. | |
| 2020/0405166 A1 | 12/2020 | Wu et al. | |
| 2021/0145342 A1 | 5/2021 | Wang | |
| 2021/0187246 A1 | 6/2021 | Houck | |
| 2021/0204871 A1 | 7/2021 | Goedeke et al. | |
| 2021/0268234 A1 | 9/2021 | Helgeson et al. | |
| 2021/0298656 A1 | 9/2021 | Wu et al. | |
| 2021/0361216 A1 | 11/2021 | Hoitink et al. | |
| 2021/0401345 A1 | 12/2021 | Wu et al. | |
| 2022/0023594 A1 | 1/2022 | Pai | |
| 2022/0054066 A1 | 2/2022 | Solis | |
| 2022/0061727 A1 | 3/2022 | Olson et al. | |

FOREIGN PATENT DOCUMENTS

| | | | |
|---|---|---|---|
| CN | 103157168 B | 4/2015 | |
| CN | 106859765 A | 6/2017 | |
| CN | 206880930 U | 1/2018 | |
| CN | 104958824 B | 12/2018 | |
| CN | 104434083 B | 4/2019 | |
| CN | 104968261 B | 5/2019 | |
| CN | 105592778 B | 7/2019 | |
| CN | 111657866 A | 9/2020 | |
| CN | 106264715 B | 11/2020 | |
| CN | 106264716 B | 11/2020 | |
| CN | 106308790 B | 6/2021 | |
| CN | 107529958 B | 7/2021 | |
| CN | 109310469 B | 7/2021 | |
| CN | 109641121 B | 9/2021 | |
| CN | 109952123 B | 9/2021 | |
| CN | 110559544 B | 9/2021 | |
| CN | 113425304 A | 9/2021 | |
| CN | 105615994 B | 10/2021 | |
| CN | 109963610 B | 11/2021 | |
| CN | 108289709 B | 3/2022 | |
| EP | 0889744 B1 | 1/2004 | |
| EP | 1723981 A1 | 11/2006 | |
| EP | 1254641 B1 | 11/2008 | |
| EP | 1690564 B1 | 4/2009 | |
| EP | 1723981 B1 | 8/2010 | |
| EP | 2135634 B1 | 10/2011 | |
| EP | 2018203 B1 | 6/2012 | |
| EP | 1814450 B1 | 1/2013 | |
| EP | 2269532 B1 | 3/2013 | |
| EP | 2630986 A2 * | 8/2013 | ......... A61B 5/04001 |
| EP | 2604306 B1 | 1/2014 | |
| EP | 2915555 A1 | 9/2015 | |
| EP | 1968679 B1 | 9/2016 | |
| EP | 2241279 B1 | 9/2016 | |
| EP | 3115076 A4 | 10/2017 | |
| EP | 3117863 A4 | 10/2017 | |
| EP | 3111871 B1 | 3/2018 | |
| EP | 3111872 B1 | 4/2018 | |
| EP | 3057488 B1 | 5/2018 | |
| EP | 2848226 B1 | 7/2018 | |
| EP | 3363397 A1 | 8/2018 | |
| EP | 3391928 A1 | 10/2018 | |
| EP | 3122276 B1 | 11/2018 | |
| EP | 3398549 A1 | 11/2018 | |
| EP | 1759668 B1 | 12/2018 | |
| EP | 3037122 B1 | 12/2018 | |
| EP | 2234537 B1 | 1/2019 | |
| EP | 2569040 B1 | 2/2019 | |
| EP | 3023052 B1 | 3/2019 | |
| EP | 3466363 A1 | 4/2019 | |
| EP | 2550989 B1 | 6/2019 | |
| EP | 3512589 A1 | 7/2019 | |
| EP | 3512590 A1 | 7/2019 | |
| EP | 3527125 A1 | 8/2019 | |
| EP | 3531903 A1 | 9/2019 | |
| EP | 3434218 B1 | 2/2020 | |
| EP | 2908723 B1 | 3/2020 | |
| EP | 3114987 B1 | 8/2020 | |
| EP | 3178516 B1 | 9/2020 | |
| EP | 3738508 A1 | 11/2020 | |
| EP | 3738509 A1 | 11/2020 | |
| EP | 3340916 B1 | 12/2020 | |
| EP | 3750475 A1 | 12/2020 | |
| EP | 2155301 B1 | 4/2021 | |
| EP | 3432820 B1 | 4/2021 | |
| EP | 2809254 B1 | 6/2021 | |
| EP | 3508245 B1 | 7/2021 | |
| EP | 3858277 A1 | 8/2021 | |
| EP | 3791820 B9 | 4/2022 | |
| JP | 4545384 B2 | 7/2010 | |
| JP | 2010167101 A | 8/2010 | |
| JP | 4887810 B2 | 2/2012 | |
| JP | 4940332 B2 | 3/2012 | |
| JP | 2012055602 A | 3/2012 | |
| JP | 2012200509 A | 10/2012 | |
| JP | 5154031 B2 | 2/2013 | |
| JP | 5193190 B2 | 5/2013 | |
| JP | 2013-543743 A | 12/2013 | |
| JP | 5372314 B2 | 12/2013 | |
| JP | 2014-501557 A | 1/2014 | |
| JP | 2014014713 A | 1/2014 | |
| JP | 5550150 B2 | 5/2014 | |
| JP | 5762697 B2 | 6/2015 | |
| JP | 5856712 B2 | 2/2016 | |
| JP | 5908270 B2 | 4/2016 | |
| JP | 5944331 B2 | 7/2016 | |
| JP | 2016525914 A | 9/2016 | |
| JP | 6050522 B2 | 12/2016 | |
| JP | 2017051211 A | 3/2017 | |
| JP | 2017104552 A | 6/2017 | |
| JP | 6246742 B2 | 12/2017 | |
| JP | 6342524 B2 | 6/2018 | |
| JP | 6434495 B2 | 12/2018 | |

(56) References Cited

FOREIGN PATENT DOCUMENTS

| | | | |
|---|---|---|---|
| JP | 6445509 | B2 | 12/2018 |
| JP | 6445742 | B1 | 12/2018 |
| JP | 6466114 | B2 | 2/2019 |
| JP | 6515084 | B2 | 4/2019 |
| JP | 6528010 | B1 | 5/2019 |
| JP | 6655655 | B2 | 2/2020 |
| JP | 6776021 | B2 | 10/2020 |
| JP | 6776025 | B2 | 10/2020 |
| JP | 6786275 | B2 | 11/2020 |
| JP | 6821812 | B2 | 1/2021 |
| JP | 2021007772 | A | 1/2021 |
| JP | 6843502 | B2 | 3/2021 |
| JP | 6920312 | B2 | 8/2021 |
| JP | 6926306 | B2 | 8/2021 |
| JP | 6932484 | B2 | 8/2021 |
| JP | 6980386 | B2 | 11/2021 |
| JP | 2022020838 | A | 2/2022 |
| WO | 9843530 | A1 | 10/1998 |
| WO | 0168178 | A1 | 9/2001 |
| WO | 2008091197 | A1 | 7/2008 |
| WO | 2009/120982 | A2 | 10/2009 |
| WO | WO-2015116692 | A1 * | 8/2015 ......... A61B 18/1492 |
| WO | 2016/112196 | A1 | 7/2016 |
| WO | 2017098198 | A1 | 6/2017 |
| WO | 2018053148 | A1 | 3/2018 |
| WO | 2018053164 | A1 | 3/2018 |
| WO | 2018136741 | A1 | 7/2018 |

\* cited by examiner

SHEATH VISUALIZATION

CROSS-REFERENCE TO RELATED APPLICATIONS

This application is a U.S. National Stage of PCT/US2018/014430 filed Jan. 19, 2018; which claims the benefit of U.S. provisional application No. 62/447,967, filed 19 Jan. 2017 (the '967 application), which is hereby incorporated by reference as though fully set forth herein.

BACKGROUND OF THE INVENTION a. Field of the Invention

This disclosure relates to a family of medical devices. More particularly, this disclosure relates to medical devices, such as, for example, catheters or sheaths, having one or more electrodes mounted thereon for electrophysiology (EP) diagnostics and localization and visualization of said devices, where additive manufacturing has been used to create at least a portion of the electrically conductive components.

b. Background Art

It is well known to use a medical device called a sheath or catheter when performing various therapeutic and/or diagnostic medical procedures on or in the heart, for example. Once inserted into a patient's body sheaths provide a path through a patient's vasculature to a desired anatomical structure or site for a second medical device, such as, for example, a catheter, a needle, a dilator, etc., and also allow for the proper positioning or placement of the second medical device relative to the desired anatomical structure. A catheter can also be inserted into a patient's body and moved to a desired anatomical structure or site. The catheter can then perform diagnostic, ablative, or other procedures.

One drawback to conventional sheaths and their use is that visualization of the sheath and/or its position has proved difficult, if not impossible. As a result, physicians have been unable to see the sheath and/or its position during the performance of a medical procedure without the use of ionizing radiation (e.g., acute x-ray delivery via a fluoroscope). However, with the advent and growing use of various automated guidance systems, such as, for example, magnetic-based and robotic-based guidance systems, the need for such visualization capability has increased.

In addition to the need of visualization in the use of automated guidance systems, the need for this capability is also increasing in instances where a physician manually controls medical devices. For example, for procedures performed on the left side of the heart, a transseptal puncture is used to cross the septum separating the right atrium from the left atrium. In such procedures, a long, small diameter needle is passed down a lumen in the sheath and is used to puncture the septal wall. Once formed, the sheath is inserted into the hole created by the puncture operation and crosses through the septum, thereby providing another medical device within the sheath access to the left atrium. Using current visualization systems, such as, for example, fluoroscopy, the transseptal crossing point (and the sheath therein) is invisible to the physician. Accordingly, if the physician loses visual contact with a device or the transseptal access is interrupted due to, for example, patient movement or the manipulation of a medical device used with the sheath, regaining access increases the procedure time and also can require another puncture of the septum. Because there is no visualization of the sheath, or any representation of the sheath on a display the physician is using, the physician has no reference to help guide him to regain access.

Further, catheters and sheaths with components for visualization, diagnostic, or other procedures electrically connected to a proximal end of the medical device by conductive wires passing through the medical device can be costly and time consuming to manufacture.

Accordingly, the inventors herein have recognized a need for sheath and catheter designs and methods of manufacturing that minimize and/or eliminate one or more of the deficiencies in conventional sheaths and catheters.

BRIEF SUMMARY OF THE INVENTION

In one embodiment, a medical device can comprise a sheath body comprising an inner wall, an outer wall, and a central major lumen extending through the sheath body along a longitudinal axis, wherein the central major lumen is defined by the inner wall, at least one outer lumen extending through said sheath body. The at least one outer lumen can be disposed between the inner wall and the outer wall. The medical device can further comprise at least one electrode coupled to a distal portion of said sheath body, at least one electrical trace, wherein each of the at least one electrodes is coupled to at least one electrical trace, and wherein the electrical trace is disposed between the inner wall and the outer wall, at least one deflection element extending through said sheath body, and an actuator coupled to a proximal end of the sheath body and wherein, the actuator is further coupled to the at least one deflection member and capable of deflecting a distal end of the catheter-introducer.

In another embodiment, a sheath can comprise an inner liner, an outer layer, at least one spaghetti tube, at least one pullwire, and a plurality of electrical traces, wherein the inner liner comprises an inner wall, and wherein the inner wall defines a central major lumen extending through the sheath along a longitudinal axis. The at least one spaghetti tube can define a minor lumen, wherein the at least one pullwire is disposed within the minor lumen, and wherein the at least one spaghetti tube is coupled to an exterior wall of the inner liner. The sheath can further comprise a plurality of electrodes coupled to a distal portion of said sheath, wherein each of the plurality of electrodes is electrically coupled to at least one of the plurality of electrical traces, and wherein the plurality of electrical traces can be disposed within the outer layer.

The foregoing and other aspects, features, details, utilities, and advantages of the present disclosure will be apparent from reading the following description and claims, and from reviewing the accompanying drawings.

DETAILED DESCRIPTION OF EMBODIMENTS OF THE INVENTION

Figure 1:
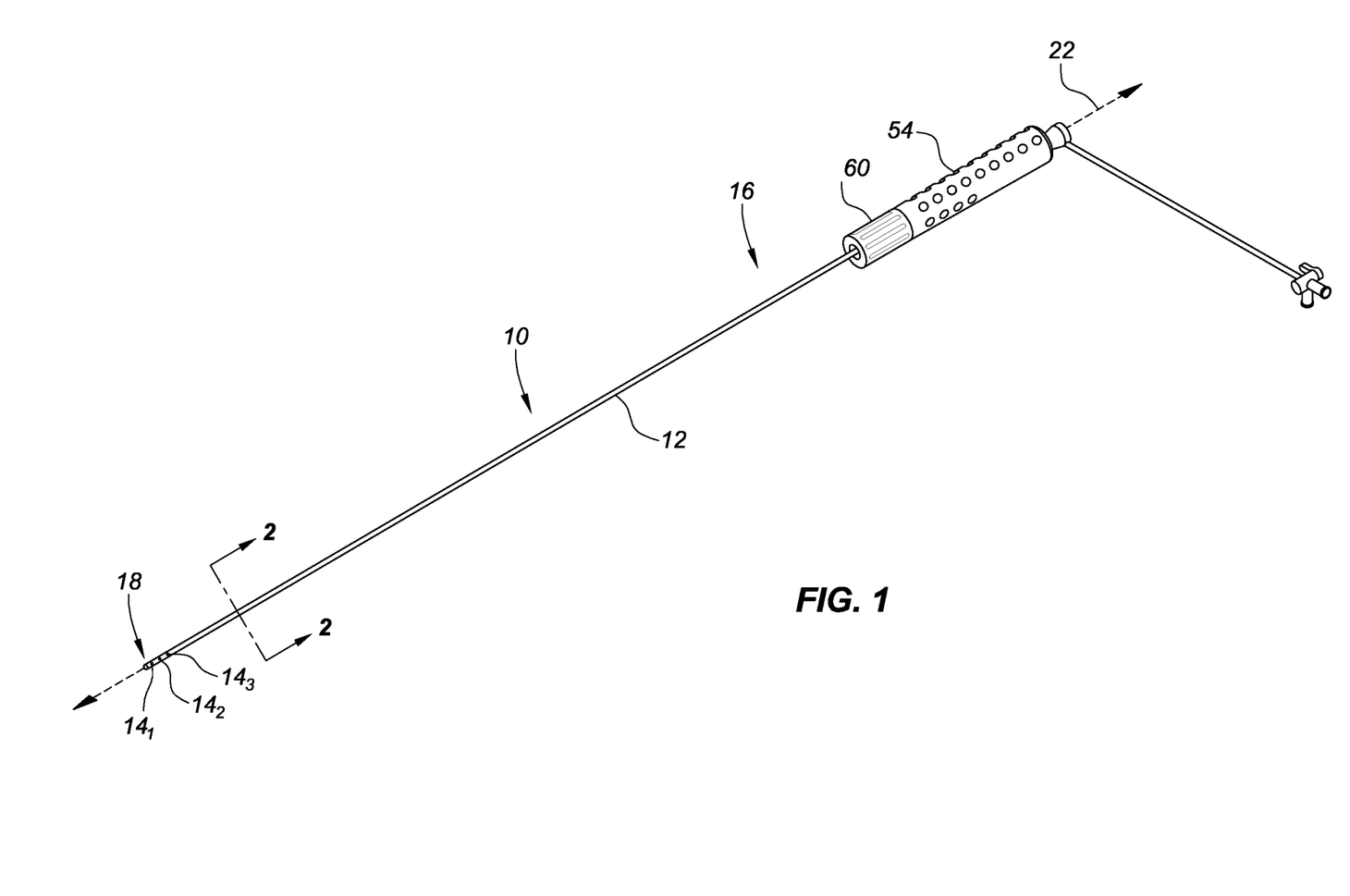
FIG. 1 is an isometric view of one embodiment of a medical device in accordance with present teachings.

Referring now to the drawings wherein like reference numerals are used to identify identical components in the various views, FIG. 1 illustrates one embodiment of a medical device 10, such as, for example and without limitation, a sheath or catheter-introducer for use in connection with a number of diagnostic and therapeutic procedures performed, for example, within the heart of a human being or an animal. For clarity and brevity purposes, the description below will be directed solely to a medical device 10 that comprises a sheath (sheath 10) for use in cardiac applications. It will be appreciated by those having ordinary skill in the art, however, that the description below can be applicable to medical devices other than sheaths, and for sheaths and medical devices used in connection with applications other than cardiac applications. Accordingly, medical devices other than sheaths, and medical devices/sheaths for use in applications other than cardiac applications, remain within the spirit and scope of the present disclosure. Further, sheaths other than deflectable sheaths also remain within the spirit and scope of the present disclosure, for example, fixed curve sheaths. Further deflectable and fixed curve catheters also remain within the spirit and scope of the present disclosure.

With reference to FIG. 1, in one embodiment, the sheath 10 comprises an elongate tubular shaft 12 and one or more electrodes 14 (e.g., $14_1$, $14_2$, $14_3$ in FIG. 1) mounted or integrated thereon. The shaft 12 has a proximal end 16, a distal end 18, and a major lumen extending between proximal and distal ends 16, 18 (as used herein, "proximal" refers to a direction toward the end of the sheath 10 near the physician/clinician, and "distal" refers to a direction away from the physician/clinician). The major lumen defines a longitudinal axis 22 of the sheath 10, and is sized to receive a medical device therein. As illustrated in FIG. 1, and as will be described in greater detail below, the electrodes 14 are mounted or otherwise coupled to the shaft 12 at the distal end 18 thereof. However, in another embodiment, one or more of the electrodes 14 can be mounted at a location on the shaft 12 more proximal than the distal end 18. Additionally, the shaft 12 can have a straight configuration, or alternatively, can have a fixed curve shape/configuration. The shaft 12 is configured for insertion into a blood vessel or another anatomic structure.

Figure 2:
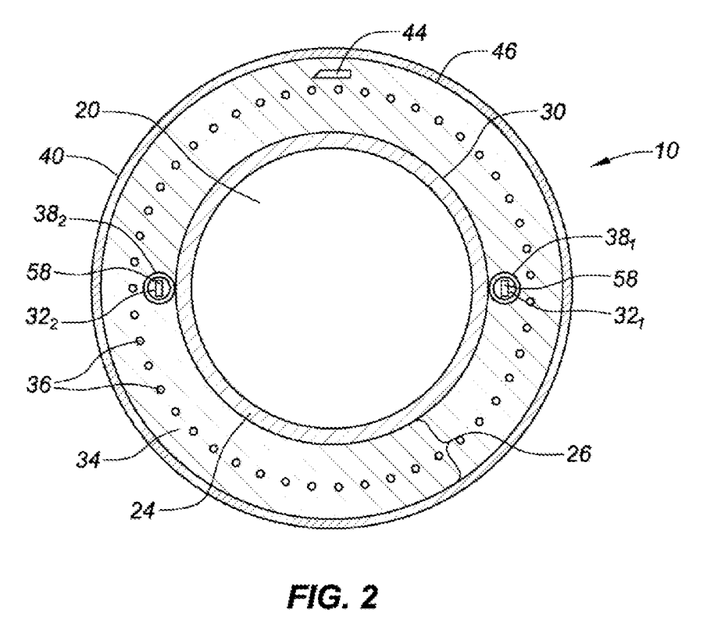
FIG. 2 is a cross-sectional view of the medical device illustrated in FIG. 1 along the line 2/2.

FIG. 2 is a cross-section view of one embodiment of the shaft 12. FIG. 2 illustrates the shaft 12 at a final stage of assembly following the performance of a reflow process on at least a portion of the shaft 12. In this embodiment, and in its most general form, the shaft 12 comprises an inner liner 24 and an outer layer 26. The shaft 12 can comprise an inner liner 24 that has an inner surface and an outer surface, wherein the inner surface defines the major lumen 20. In one embodiment, the inner liner 24 is formed of extruded polytretrafluoroethylene (PTFE) tubing, such as, for example, Teflon® tubing. In one embodiment, the PTFE comprises etched PTFE. An inner liner formed of this particular material creates a lubricious lumen (lumen 20) within which other medical devices used with the sheath 10, such as, for example, catheters, needles, dilators, and the like, can be passed. The inner liner 24 is relatively thin. For example, in one embodiment, the inner liner 24 has a thickness on the order 0.0015 inches (0.0381 mm). It will be appreciated by those having ordinary skill in the art that the inner liner 24 can be formed of a material other than PTFE, or etched PTFE. For example, in other embodiments, the inner layer is comprised of polymeric materials, such as, for example and without limitation, polyether block amides, nylon, and other thermoplastic elastomers. Accordingly, sheaths having inner liners made of materials other than PTFE remain within the spirit and scope of the present disclosure.

The shaft can further comprise an outer layer 26 that is disposed adjacent to the inner layer 24, and the outer surface 30 thereof, in particular. In one embodiment, the outer layer 26 includes one or more minor lumens $38_1$, $38_2$ therein and coupled thereto adapted to receive and house, as will be described in greater detail below, deflectable elements, such as, for example, steering or pull wires associated with a steering mechanism for the sheath 10. Each one of the one or more minor lumens $38_1$, $38_2$ defines a corresponding inner lumen 32. The outer layer 26 can further comprise at least one conductor 44 (e.g. electrical trace or film). Previous sheaths and catheters have comprised electrical wires disposed within a lumen within an outer layer or otherwise routed from an distal portion of the sheath or other medical device to a proximal end of the device. However, because of the limited size of medical devices and the large number of components that may need to be routed through the devices, manufacture of a device with electrical wires connecting components on a distal portion of the device to a more proximal location can be prohibitive in time and cost. Further, the manufacture of a device with electrical wire running therethrough can require highly skilled labor and the complex nature can cause a high number of devices that have to be scrapped during manufacture. However, using electrical traces or films as described herein can decrease cost as well as lessen the complexity of manufacturing the device. This can lead to decreased time to electrically connect components at a distal portion of the device to a more proximal portion of the device, as well as decrease the number of devices that have to be scrapped during manufacture. Because the major lumen 20 of the shaft 12 must be kept open to allow for the uninhibited passage of other medical devices therethrough, the minor lumens 38 and at least one conductor 44 are disposed within the outer layer 26 of the shaft 12. In some embodiments, some or all of the inner lumens 32 that house electrical wires associated with the electrodes 14 (i.e., lumens $32_1$, $32_2$ in FIG. 2) extend from the proximal end 16 of the shaft 12 to the distal end 18.

The outer layer 26 can be formed of a single polymeric material, or alternatively, a combination of different components/materials (e.g., various tubing and braid assemblies) that, after the application of a reflow process on at least a portion of the shaft 12, combine to form the outer layer 26. In one embodiment, the outer layer 26 comprises one or more layers of polymeric material that are placed over the inner liner. The polymeric material can comprise a tracing support as discussed below, or the polymeric material can be in the form of one or more extruded polymer tube(s) sized so as to fit over the inner layer. The tracing support or the polymer tube can comprise one or more of any number of polymeric materials, such as, for example and without limitation, polyether block amides (e.g., Pebax®), polyamides (e.g., nylon), PTFE, etched PTFE, and other thermoplastic elastomers.

The polymer tube can be formed of a single piece of tubing or multiple pieces of tubing. Whether formed of a single piece or multiple pieces, the tube can have a uniform hardness or durometer throughout. Alternatively, different portions of the tube can have different durometers (e.g., the shaft 12 can have a variable durometer from the proximal end 16 to the distal end 18). In an embodiment wherein the tube is formed of multiple pieces, the pieces can be affixed together end to end, or portions of adjacent pieces can overlap each other. These pieces can be coupled or bonded together to form the outer layer 26 during a reflow process performed thereon. Additionally, in one embodiment, one or more portions of the tube disposed at the distal end 18 of the shaft 12, or at any other location on the shaft 12 at or near where an electrode 14 is mounted or otherwise disposed, are formed so as to be translucent or transparent.

The outer layer can further comprise a braided wire assembly 36 disposed adjacent to and between both the inner liner 24 and an external surface 46 of the sheath 10. In one embodiment, the arrangement and configuration of the braided wire assembly 36 and the outer layer 26 is such that the polymeric material of the tube or tracing support melts and flows into the braid of the braided wire assembly 36 during a reflow process performed on the shaft 12. In another embodiment, the arrangement and configuration of the braided wire assembly 36 and the outer layer 26 is such that the polymeric material of the tube or tracing support melts and flows into a portion exterior the braid of the braided wire assembly 36 during a reflow process performed on the shaft 12. In this embodiment, the reflowed outer layer does not flow as deep as the braid is situated within the shaft. The braided wire assembly 36, which can extend the entire length of the shaft 12 (i.e., from the proximal end 16 to the distal end 18) or less than the entire length of the shaft 12, maintains the structural integrity of the shaft 12, and also provides an internal member to transfer torque from the proximal end 16 to the distal end 18 of the shaft 12.

In one embodiment, the braided wire assembly 36 comprises a stainless steel braid wherein each wire of the braid has a rectangular cross-section with the dimensions of 0.002 inches×0.006 inches (0.051 mm×0.152 mm). It will be appreciated by those having ordinary skill in the art, however, that the braided wire assembly can be formed of material other than, or in addition to, stainless steel. For example, in another embodiment, the braided wire assembly comprises a nickel titanium (also known as Nitinol) braid. Additionally, the braided wire assembly can have dimensions or wire sizes and cross-sectional shapes other than those specifically provided above, such as, for example, a round or circular cross-sectional shape, and also include varying braid densities throughout. Different braid wire sizes allow different shaft torque and mechanical characteristics. Accordingly, braided wire assemblies comprising materials other than stainless steel, and/or dimensions other than those set forth above, remain within the spirit and scope of the present disclosure.

As briefly described above, in one embodiment, the outer layer 26 further includes one or more minor lumens 38₁, 38₂ disposed therein and coupled thereto. Each minor lumen is adapted to receive and house a deflectable element, such as a pull wire 58, of the steering mechanism of the sheath 10. In one embodiment, the sheath 10 includes one or more extruded tubes, each one of which defines a corresponding minor lumen. The tubes, which are also known as spaghetti tubes, can be formed of a number of materials known in the art, such as, for example and without limitation, PTFE. In one embodiment, the tubes are formed a material having a melting point higher than that of the material in polymer tube so that the tubes will not melt when the shaft is subjected to a reflow process, The tubes can be affixed or bonded to the outer surface 30 of the inner layer 24. The tubes can be affixed in a number of ways, such as, for example, using an adhesive. One suitable adhesive is cyanoacrylate. Once the shaft 12 is subjected to a reflow process, the polymeric material of the tube surrounds and encapsulates the spaghetti tubes resulting in the spaghetti tubes, and therefore the minor lumens, being disposed within the outer layer of the shaft.

The minor lumens extend axially relative to the longitudinal axis 22 of the sheath 10. Minor lumens that house the pull wires 58 of the steering mechanism of the sheath 10 can extend from the proximal end 16 of the shaft 12 to the distal end 18. Alternatively, they can extend from the proximal end 16 to a point in the shaft 12 that the pull wire is coupled to another component of the steering mechanism.

In addition to the above, in one embodiment, the shaft 12 of the sheath 10 can further include a layer of heat shrink material 40 on the outer surface thereof. The heat shrink material 40 is disposed adjacent to the polymeric material of the outer layer 26 such that the outer layer 26 is disposed between the inner liner 24 and the heat shrink material 40. The heat shrink material 40 can be formed of a number of different types of heat shrink materials. In one embodiment, the heat shrink material comprises a fluoropolymer or polyolefin material, and more particularly, a tube formed of such a material sized to fit over the outer layer 26 of the shaft 16. One example of a suitable material for the heat shrink layer is fluorinated ethylene propylene (FEP).

One purpose of the heat shrink material 40 relates to the manufacturing process of the sheath 10. More particularly, during manufacture, the shaft 12 is subjected to a heat treating process, such as, for example, a reflow process. During this process, the heat shrink material 40 is caused to shrink when exposed to a suitable amount of heat. The heat applied to the shaft 12 also causes the polymeric material of the polymer tube to melt, and the shrinking of the heat shrink material forces the polymeric material to flow into contact with the inner liner 24 and tubes (in an embodiment of the sheath 10 that includes the tubes 38), as well as to flow into the braided wire assembly 36 of the shaft 12 (in an embodiment of the sheath 10 that includes the braided wire assembly). In one embodiment, the heat shrink material 40 remains as the outermost layer of the shaft 12. However, in another embodiment, the heat shrink material 40 is removed following the reflow process, and therefore, the polymer tube is the outermost layer of the shaft 12. Accordingly, sheaths 10 that when fully assembled have a heat shrink material 40, and sheaths that when fully assembled do not have a heat shrink material 40, both remain within the spirit and scope of the present disclosure.

In one embodiment, the shaft 12 can further include a lubricious coating (not shown) that can cover the entire shaft 12 and the electrodes 14 mounted thereon, or just a portion thereof. In one embodiment, the coating comprises siloxane. However, in other embodiments, the coating can comprise one of any number of suitable hydrophilic coatings such as, for example, Hydromer® or Hydak® coatings. The purpose of the lubricious coating, which can be adjacent to either the polymer tube or the heat shrink layer (if the shaft 12 has a heat shrink layer), is to provide the shaft 12 with a smooth and slippery surface that is free of sharp edges, such that the shaft can move with ease when inserted into an anatomical structure.

As briefly described above, and as will be described in greater detail below, the sheath 10 includes one or more electrodes 14 mounted or otherwise integrated to the shaft 12. As illustrated in FIG. 1, the electrodes 14 can be disposed at or near the distal end 18 of the shaft 14, and can have a number of spacing configurations. In addition, or alternatively, one or more electrodes 14 can be disposed more proximally from the distal end 18. As will be described in greater detail below, in one embodiment, the shaft 12 is deflectable. In such an embodiment, the electrodes 14 can be mounted on deflectable portions of the shaft 12 and/or non-deflectable portions. In one embodiment, the electrodes 14 are flush with the outer surface of the shaft 12, and therefore, are recessed into the shaft 12.

The electrodes 14 can comprise any number of types of electrodes and can be used for any number of purposes. For example, the electrodes 14 can comprise one or more of additively manufactured or otherwise deposited electrodes, magnetic coil(s), ring electrodes, tip electrodes, or a combination thereof. Further, the electrodes 14 can be used for a number of purposes or to perform one or more functions. For example, the electrodes 14 can be used in the pacing of the heart, monitoring electrocardiograph (ECG) signals, detecting location/position of the electrode 14 and therefore the sheath 10, mapping, visualization of the sheath 10, and the like. Additionally, one or more of the electrodes 14 can be formed of a radiopaque material, such as, for example and without limitation, a metallic material, such as, for example, platinum or another dense material. This permits the visualization of the electrodes 14 by an x-ray based visualization system, such as, for example, a fluoroscopic system.

In another embodiment of the sheath 10 a flexible circuit comprising one or more electrical conductors is disposed within the outer surface 26. The flexible circuit 46 can extend from the proximal end 16 of the shaft 12 to the distal end 18. Alternatively, the flexible circuit can extend from the proximal end 16 to the point on the shaft 12 at which the electrode(s) are coupled. The flexible circuit is configured for electrical coupling with one or more of the electrodes 14.

It will be appreciated by those having ordinary skill in the art that but for the description relating to the minor lumens being disposed within the outer layer of the shaft 12, the description above relating to the construction and composition of the shaft 12 applies with equal force to an embodiment wherein the shaft 12 includes a flexible circuit disposed therein.

In one embodiment, the sheath 10 can be steerable (i.e., the distal end 18 of the shaft 12 can be deflected in one or more directions relative to the longitudinal axis 22 of the sheath 10). In one embodiment, the movement of the sheath 10 can be controlled and operated manually by a physician. In another embodiment, however, movement of the sheath 10 can be controlled and operated by an automated guidance system, such as, for example and without limitation, a robotic-based system or a magnetic-based system.

In one embodiment wherein the sheath 10 is configured for physician control, the sheath 10 includes a steering mechanism. A detailed description of one steering mechanism, such as steering mechanism, is set forth in U.S. Patent Publication No. 2007/0299424 entitled "Steerable Catheter Using Flat Pull Wires and Method of Making Same" filed on Dec. 29, 2006, the disclosure of which is hereby incorporated by reference in its entirety. Accordingly, with reference to FIGS. 1 and 2, the steering mechanism will be briefly described. In one embodiment, the steering mechanism comprises a handle 54, a pull ring 56 disposed in the shaft 12 of the sheath 10, and one or deflection elements, such as pull wires 58, coupled with both the handle 54 and the pull ring 56, and disposed within the shaft 12 of the sheath 10.

As illustrated in FIG. 1, the handle 54 is coupled to the shaft 12 at the proximal end 16 thereof. In one embodiment, the handle 54 provides a location for the physician/clinician to hold the sheath 10 and, in one embodiment, is operative to, among other things, effect movement (i.e., deflection) of the distal end 18 of the shaft 12 in one or more directions. The handle 54 is conventional in the art and it will be understood that the construction of the handle 54 can vary.

In one embodiment, the handle 54 includes an actuator 60 disposed thereon or in close proximity thereto, that is coupled to the pull wires 58 of the steering mechanism. The actuator 60 is configured to be selectively manipulated to cause the distal end 18 to deflect in one or more directions. More particularly, the manipulation of the actuator 60 causes the pull wires 58 to be pushed or pulled (the length of the pull wires is increased or decreased), thereby effecting movement of the pull ring 56, and thus, the shaft 12. The actuator 60 can take a number of forms known in the art. For example, the actuator 60 can comprise a rotatable actuator, as illustrated in FIG. 1, that causes the sheath 10, and the shaft 12 thereof, in particular, to be deflected in one direction when rotated one way, and to deflect in another direction when rotated in the other way. Additionally, the actuator 60 can control the extent to which the shaft 12 is able to deflect. For instance, the actuator 60 can allow the shaft 12 to deflect to create a soft curve of the shaft. Additionally, or in the alternative, the actuator 60 can allow the shaft 12 to deflect to create a more tight curve (e.g., the distal end 18 of the shaft 12 deflects 180 degrees relative to the shaft axis 22). It will be appreciated that while only a rotatable actuator is described in detail here, the actuator 60 can take on any form known the art that effects movement of the distal portion of a sheath or other medical device.

The actuator 60 is coupled to the pull wires 58 of the steering mechanism. In one embodiment, the pull wires 58 are located within the outer layer 26 of the shaft 12. More particularly, the pull wires 58 are disposed within the minor lumens $38_1$, $38_2$ in the outer layer, and are configured to extend from the handle 54 to the pull ring 56 (best shown in FIG. 3). In one embodiment, the pull wires 58 have a rectangular cross-section. In other embodiments, however, the pull wires 58 can have a cross-sectional shape other than rectangular, such as, for example and without limitation, a round or circular cross-sectional shape.

The steering mechanism can comprise a number of different pull wire arrangements. For instance, the steering mechanism can includes four pull wires 58. In that embodiment, the pull wires 58 are disposed 90 degrees apart from each other. In another embodiment, the steering mechanism comprises two pull wires 58. In such an embodiment, the pull wires 58 are spaced 180 degrees apart from each other.

Figure 3:
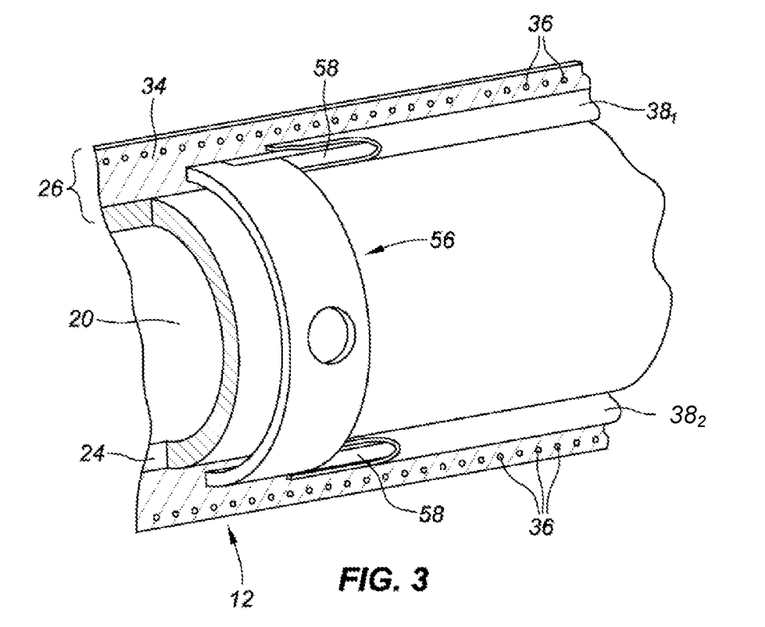
FIG. 3 is a cut-away perspective view of a portion of the medical device illustrated in FIG. 1.

The pull wires 58 are coupled at a first end to the actuator 60 and at the second end to the pull ring 56. FIG. 3 is a depiction of a portion of the shaft 12 having the outer layer 26 surrounding the pull ring 56 cut away. As illustrated in FIG. 3, the pull ring 56 is anchored to the shaft 12 at or near the distal end 18 thereof. One means by which the pull ring 56 is anchored is described in U.S. Patent Publication No. 2007/0199424 entitled "Steerable Catheter Using Flat Pull Wires and Method of Making Same" filed on Dec. 29, 2006, the entire disclosure of which was incorporated by reference above. Accordingly, as the pull wires 58 are pulled and/or pushed, the pull wires 58 pull and push the pull ring 56, thereby causing the shaft 12 to move (e.g., deflect). Accordingly, the physician manipulates the actuator 60 to cause the distal end 18 of the shaft 12 to move in a certain direction. The actuator 60 pulls and/or pushes the correct pull wires 58, which then causes the pull ring 56, and therefore the shaft 12, to move as directed.

As briefly described above, in another embodiment, rather than being configured for manual control, the sheath 10 is controlled by an automated guidance system. In one embodiment the automated guidance system is a robotic system. In such an embodiment, the sheath 10 includes a steering mechanism that is coupled with the robotic system and acts in concert with, and under the control of, the robotic system to effect movement of the distal end 18 of the shaft 12. Detailed descriptions of arrangements/configurations by which a robotic system controls the movement of a medical device are set forth in PCT Patent Application Serial No. PCT/2009/038597 entitled "Robotic Catheter System with Dynamic Response" filed on Mar. 27, 2009 (International Publication No. WO/2009/120982), and U.S. Patent Publication No. 2009/0247993 entitled "Robotic Catheter System" filed on Dec. 31, 2008, the disclosures of which are hereby incorporated by reference in their entireties. In such an embodiment, the control devices are controlled by a controller, which, in turn, can be fully automated and/or responsive to user inputs relating to the driving or steering of the sheath 10.

While the description of an automated sheath control system has been with respect to one particular robotic system, other automated guidance systems and other types of robotic systems can be used. Accordingly, automated guidance systems other than robotic systems, and robotic-based automated guidance systems other than that described with particularity above, remain within the spirit and scope of the present disclosure.

Figure 4:
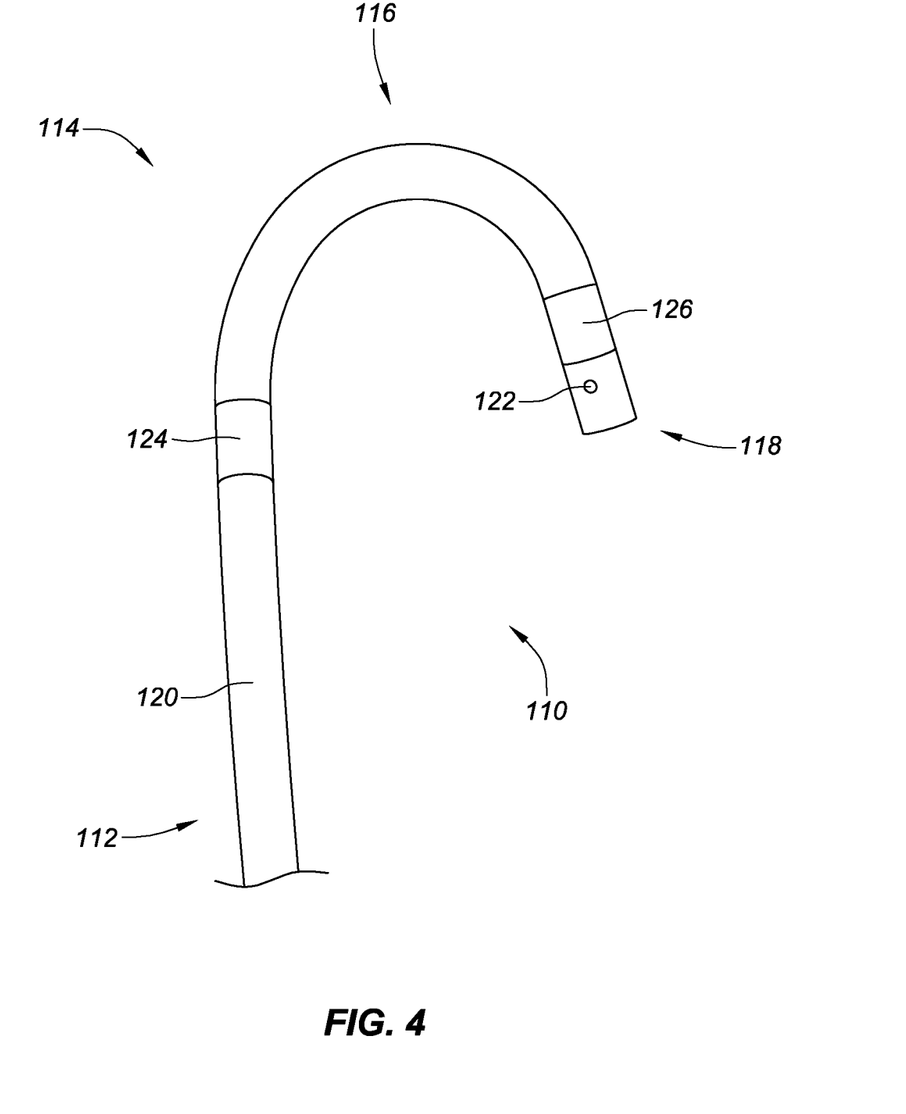
FIG. 4 is a side view of one embodiment of a medical device in accordance with present teachings

FIG. 4 illustrates a side view of another embodiment of a sheath 110 according to the disclosure. The sheath 110 comprises a sheath body 120, a distal end 114, a first electrode 124, a second electrode 126, a distal tip 118, and an aspiration hole 122. The first electrode 124 and the second electrode 126 can be coupled to the sheath body 120. In another embodiment, the first electrode 124 and the second electrode 126 can be integral to the sheath body 120. In this embodiment, the first electrode 124 and the second electrode 126 can be integrated within the sheath body 120 as described herein. The sheath body 120 can comprise multiple layers as described throughout this application that can be reflowed together or otherwise coupled to each other. The outermost layer of the sheath body 120 can comprise a material with electrical tracing embedded in or printed on top of the material. This material can then be coupled or reflowed to the sheath 110. The sheath 110 can further comprise a straight portion 112 and a curved portion 116. The first electrode 124 can be disposed on the straight portion 112 of the sheath 110 and proximal of the curved portion 116 and the second electrode 126. The second electrode 126 can be disposed adjacent the distal tip 118 and proximal of the aspiration hole 122. The aspiration hole 122 can comprise a through-hole extending from an outer surface of the sheath body 120 to an inner surface of the sheath body 120. The inner surface of the sheath body 120 can define a lumen that extends from the distal tip 118 of the sheath 110 to a proximal end of the sheath 110. The aspiration hole 122 can allow for fluid to move from the lumen of the sheath to an exterior portion of the sheath when a second medical device is being moved through, or extending from the distal end of the lumen of the sheath.

Figure 5A:
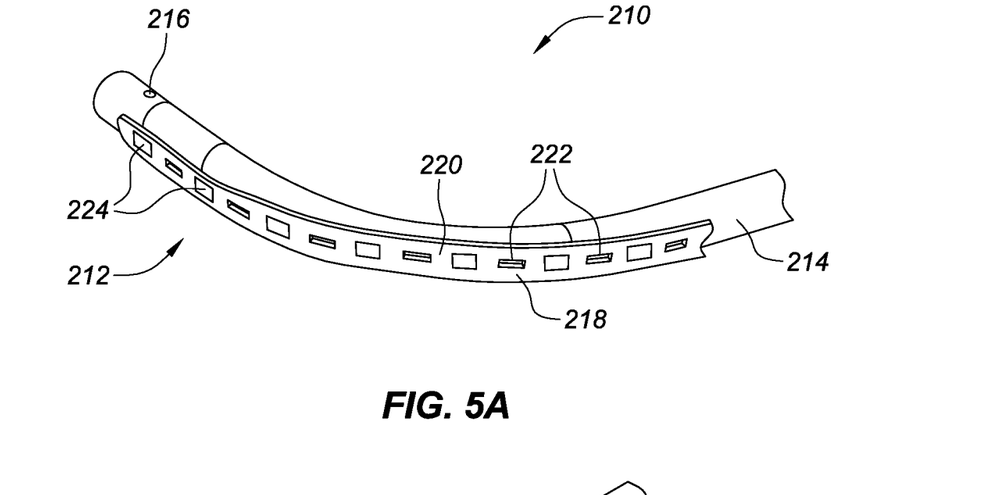
FIGS. 5A and 5B are isometric views of one embodiment of a medical device comprising a tracing support.

FIG. 5A illustrates an isometric view of one embodiment of a sheath 210 as described herein. The sheath 210 can comprise a sheath body 214, a distal end portion 212, and an aspiration hole 216. The sheath body 214 can comprise and inner layer and an outer layer as discussed above. The outer layer can comprise a tracing support 218. The tracing support 218 can comprise a base material 220, a plurality of electrode sites 224, a plurality of gaps 222, and a plurality of conductors (not shown). The base material 220 can comprise a material that can accept an electrically traced, photo etched, or additive manufacturing process to add electrically conductive material to the base material. In some embodiments, the base material 220 can further comprise a material that can be reflowed or a reflowable material. In some embodiments, the base material 220 can comprise polyurethane, pebax, nylon blends, liquid crystal polymer, polyamides, or other materials that would be known to one of ordinary skill in the art to be reflowable or able to be reflowed. In some embodiments, the use of polyamide for the base material can be excluded as the stiffness of polyamide can increase manufacturing cost and difficulty. The plurality of electrodes and the plurality of conductors can be added to the base material while the base material is flat or otherwise not in the final arrangement seen in the sheath. In some embodiments, each of the plurality of electrodes can be coupled to an individual conductor. Each of the plurality of conductors can then run in a proximal direction from the electrode that conductor is coupled to, to a proximal end of the sheath. In other embodiments, each of the plurality of conductors can run in a proximal direction along the tracing support and can each couple to a separate conductor at a more proximal location along the sheath. In some embodiments, after the plurality of electrodes and the plurality of conductors have been added to the tracing support through one of the processes described above, an additional layer of material can be added on top of the plurality of conductors to seal or otherwise block the conductors from exposure to interference or other interaction with materials or substances exterior the tracing support. In another embodiment, the additional layer of material can also cover an outside portion of the plurality of electrode sites.

After the electrically conductive material has been added to the base material, the tracing support 218 can be rolled and placed over and around the exterior of the sheath. The tracing support 218 can then be coupled to the exterior of the sheath. The tracing support 218 can be coupled through adhesive or the tracing support can be reflowed over the sheath. In embodiments where adhesive is used to couple the tracing support to the sheath, the adhesive can comprise cyanoacrylates, epoxies, or other adhesives as would be known to one of ordinary skill in the art. In one embodiment, the tracing support can entirely surround an exterior circumference of the sheath. In other embodiments, the tracing support can surround only a portion of the sheath. As illustrated in FIG. 4, the tracing support can cover a portion of an exterior circumference of the sheath, and can then be integrated or otherwise comingled with the sheath through a reflow process. By reflowing the tracing support on to the sheath, the sheath can comprise a generally circular outer circumference and remove edges that could otherwise be present from joining separate pieces or portions of the sheath. In one embodiment, the electrical conductors can be closely spaced and run along a straight or mostly straight line down the tracing support. In this embodiment, when coupling the tracing support to the sheath, the conductors running from the plurality of electrode sites to a proximal end of the tracing support can be placed along a centerline of deflection to minimize strain. This means that the electrodes can run in-between, or at a point farthest away from the deflection planes in an embodiment where the sheath can deflect in two, different directions. In one embodiment, the conductors can be placed 90 degrees along the external surface of the sheath from the deflection plane. In other embodiments, they can be placed in other portions away from the plane, or planes, of deflection. In the illustrated embodiment, the plurality of gaps 222 can be configured to allow for flexibility of the tracing support and/or to lessen the amount of material added to the sheath 210. In the illustrated embodiment, one of the plurality of gaps 222 is disposed between each of the plurality of electrodes. In other embodiments, a gap may be present in between only several of the electrodes or at portions of the sheath that will undergo greater movement than others. In one embodiment, the plurality of gaps can be disposed between the electrodes that are disposed on the portion of the sheath that deflects when the sheath is deflected. In other embodiments, the plurality of gaps can be disposed between the electrodes that are disposed on the portion of the sheath that does not deflect when the sheath is deflected. In yet other embodiments, the plurality of gaps can be excluded from the tracing support. In this embodiment, the tracing support can be continuous from a distal end to a proximal end, and no gaps as described herein can be included.

In one embodiment, the conductors can be printed on an exterior facing portion of the tracing support. When the tracing support is reflowed over the sheath, the conductors can be integrated into an interior portion of the tracing support. In another embodiment, the conductors can be printed on an exterior facing portion of the tracing support and another layer of material can be added over the tracing support. When the sheath is placed through the reflow process, the additional layer can integrate with the tracing support and underlying layers of the sheath to cover and protect the conductors. This process can embed or otherwise comingle the conductors within the sheath. In another embodiment, the conductors can be printed on an interior facing portion of the tracing support. When the tracing support is reflowed over the sheath, the conductors can be integrated into an interior portion of the tracing support. In this embodiment, the tracing support can further comprise a portion of the conductor that can pass from the interior facing portion where the conductors are disposed to an exterior facing portion where the at least one electrode described herein can be disposed. By running a portion of the conductor from the interior portion to the exterior portion, the at least one electrode can be electrically coupled to the conductor.

In another embodiment, the conductors extending from the at least one electrode to a more proximal portion of the sheath can be disposed in a spiral or helical pattern around an outer circumference of the sheath. In this embodiment, the tracing support can be manufactured so that it is configured to be wound around an exterior portion of the sheath before being coupled to the sheath. When the conductors are wound in a spiral or helical pattern, the strain on the conductors can be lessened or minimized when compared to a conductor that travels in a mostly straight line along a longitudinal axis of the sheath. In one embodiment, the tracing support can be coupled to itself to form a hollow tube sized and configured to be placed over a sheath. The tracing support can then be reflowed at a proximal end and a distal end of the sheath. By reflowing the tracing support at the proximal and distal ends of the sheath, the tracing support can be floating in between the distal end and the proximal end of the sheath. By reflowing the portions of the tracing support at the proximal end and the distal end, the floating portion in between these reflowed portions can lessen the strain on the conductors and improve durability. In another embodiment, the tracing support can be reflowed over the distal end of the sheath, and the tracing support proximal of the reflowed portion can be floating. In yet another embodiment, the distal end, the proximal end, and a middle portion of the tracing support can be reflowed over the sheath. In one embodiment, the conductors can be wound around the outer circumference of the sheath at a high pitch. In other embodiments, the conductors can be wound around the outer circumference of the sheath at a lower pitch. The pitch of the conductors can be determined by the materials and the geometry of the sheath and can be configured to be wound around the circumference at a pitch that can handle the bending strains for a particular material and geometry.

Figure 5B:
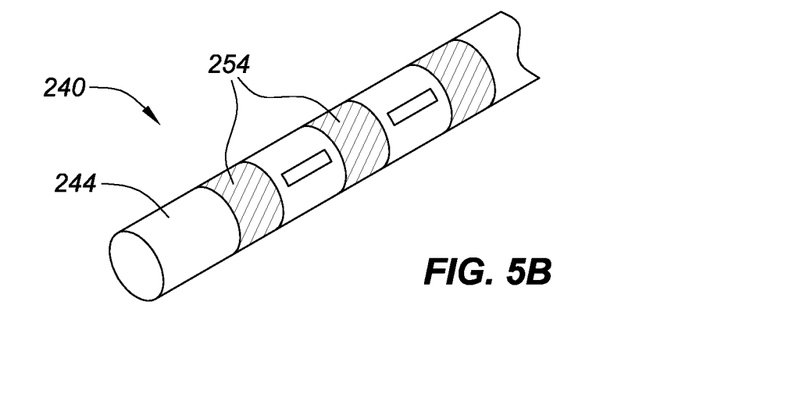

FIG. 5B illustrates the sheath of FIG. 5A after the tracing support has been rolled and reflowed on the sheath. The sheath 240 can comprise a sheath body 244 and a plurality of electrode sites 254. As seen in FIG. 5B, the tracing support is now fully integrated and coupled to the sheath.

Figure 6:
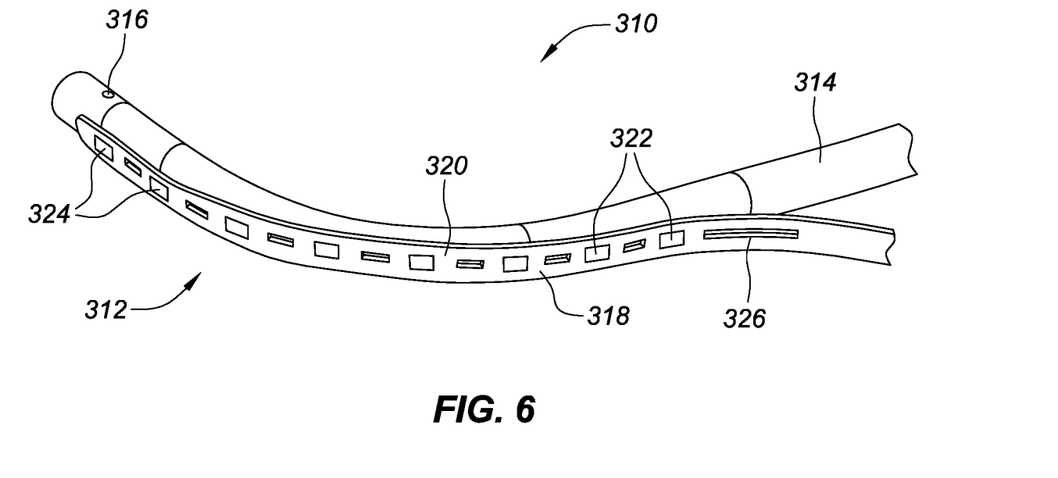
FIG. 6 is an isometric view of another embodiment of a medical device comprising a tracing support.

FIG. 6 illustrates an isometric view of another embodiment of a sheath 310 as described herein. The sheath 310 can comprise a sheath body 314, a distal end portion 312, an aspiration hole 316, and a tracing support 318. The tracing support 318 can comprise a base material 320, a plurality of electrode sites 324, a plurality of gaps 322, at least one extended gap 326, and a plurality of conductors (not shown). As stated above, the base material 320 can comprise a material that can accept an electrically traced, photo etched, or additive manufacturing process to add electrically conductive material to the base material. The tracing support of FIG. 6 further comprises at least one extended gap 326. The at least one extended gap 326 can be disposed proximal of the plurality of electrodes 324. While the illustrated embodiment depicts a single extended gap, additional extended gaps can be disposed proximal that shown. The at least one extended gap 326 can be used allow for flexibility of the tracing support and/or to lessen the amount of material added to the sheath 310. Further, other methods can be used as described herein to allow for flexibility of the tracing support and/or to lessen the amount of material added to the sheath.

Figure 7:
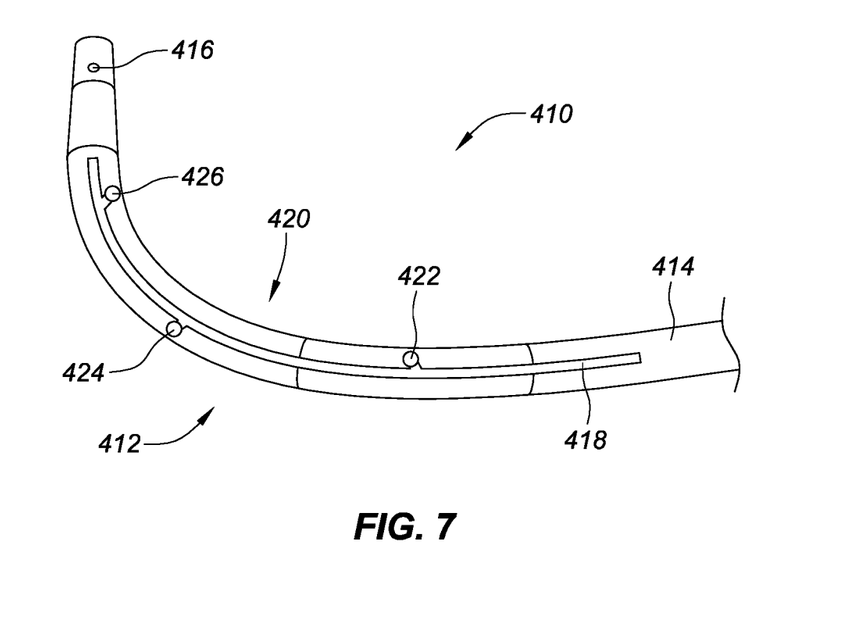
FIGS. 7 and 8 are side views of another embodiment of a medical device in accordance with present teachings in a deflected and undeflected state.
Figure 8:
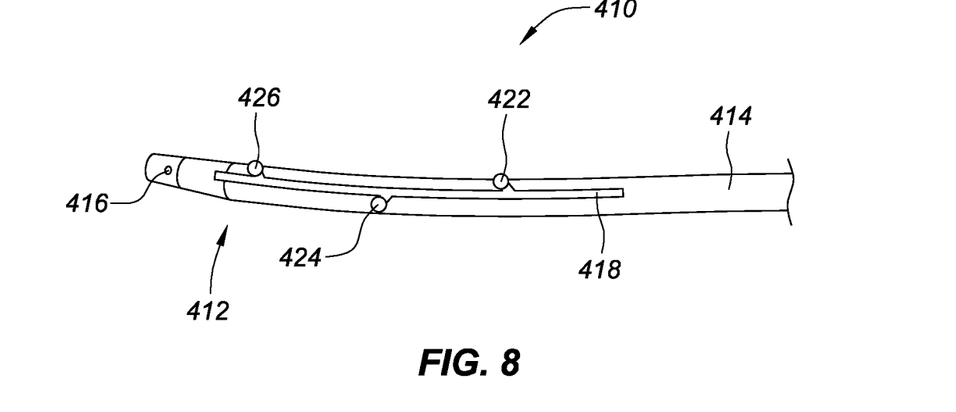

FIGS. 7 and 8 illustrate side views of another embodiment of a sheath 410 as described above. The sheath 410 of FIG. 7 is shown in a deflected state. The sheath 410 of FIG. 8 is shown in an undeflected state. The sheath 410 can comprise a sheath body 414, a distal end portion 412, a deflectable portion 420, an aspiration hole 416, a first electrode 422, a second electrode 424, a third electrode 426, and a conductor portion 418. The first electrode 422, the second electrode 424, and the third electrode 426 can be separated along a longitudinal axis of the sheath 410. The first electrode 422, the second electrode 424, and the third electrode 426 in the illustrated embodiment can comprise spot electrodes. In other embodiments, the sheath can comprise one electrode, two electrodes, or other quantities of electrodes. In yet other embodiments, the one or more electrodes disposed on the sheath can comprise ring electrodes that extend around an outer circumference of the sheath. In another embodiment, a ring electrode can be coupled to a portion of the conductor that is exposed to an exterior portion of the sheath. The ring electrode can comprise a composition that would be known to one of ordinary skill in the art and can be swaged, secured with adhesive, or otherwise coupled to the sheath so that the ring is electrically coupled to the conductor. In yet other embodiments, the one or more electrodes can comprise electrodes that extend around a portion of an outer circumference of the sheath, or can comprise spot electrodes of different shapes and sizes than those illustrated in FIGS. 7 and 8. In yet another embodiment, the electrode can comprise a tab that can be wrapped around an outer circumference of the shaft and coupled thereto. In various embodiments, the tab can be configured to extend around the entire circumference or a partial circumference of an exterior of the sheath. The tab can comprise an electrically conductive material that has been additively added to a base layer. The same process can be used as that which is discussed above in relation to the tracing support. While the illustrated embodiments show electrodes evenly spaced along the medical device, in other embodiments the electrodes can be placed in various lengths and orientations from the neutral plane. By placing the electrodes in various lengths and orientations, separate and unique 3D locations in space can be achieved to determine the centerline of the medical device for project visualization in an imaging system.

The conductor portion 418 of the sheath 410 can comprise a base material as discussed above and a plurality of conductors. The plurality of conductors can electrically connect the electrodes of the sheath to a connector or other device at a proximal end of the sheath. In the illustrated embodiment, the conductor portion can comprise a first conductor electrically coupled to the first electrode, a second conductor electrically coupled to the second electrode, and a third conductor electrically coupled to the third electrode. The plurality of conductors can then run along a neutral axis of the sheath to a more proximal location. The neutral axis of the sheath can comprise a location along an exterior circumference of the sheath that is around the same distance, in each direction, around the outer circumference from a pullwire. In one embodiment, the plurality of conductors can run to a proximal end of the sheath. In another embodiment, the plurality of conductors can run to a more proximal location of the sheath and each of the conductors can then couple to another electrical conductor that can run to a proximal end of the sheath, or to a proximal end of an actuator coupled to a proximal end of the sheath.

Figure 9A:
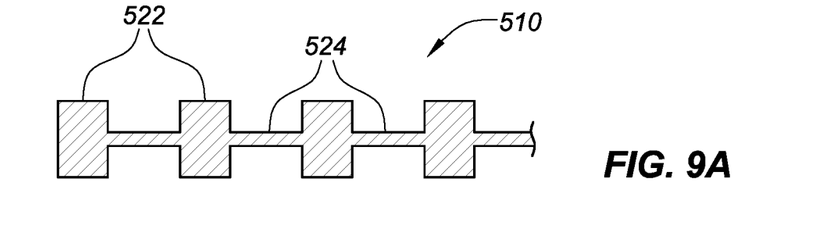
FIGS. 9A and 9B are isometric views of another embodiment of a medical device comprising a tracing support.
Figure 9B:
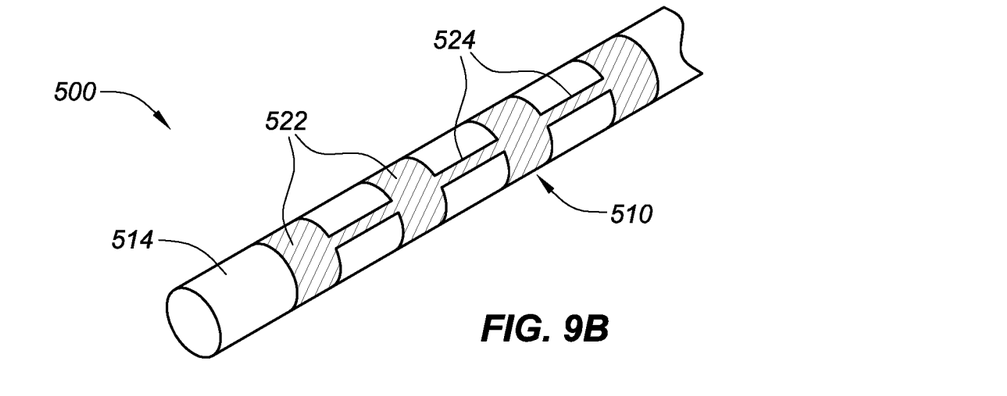

FIG. 9A depicts an isometric view of another embodiment of a tracing support 510 as described herein. The tracing support 510 can comprise a plurality of electrode sites 522 and a conductor portion 524. As described herein, the tracing support can comprise a flexible material. The tracing support 510 can be rolled and reflowed around a sheath as described herein. FIG. 9B illustrates an isometric view of the tracing support of FIG. 9A after it has been rolled and reflowed onto a sheath. The sheath 500 can comprise a sheath body 514 and a tracing support 510. The tracing support can comprise a plurality of electrode sites 522 and a conductor portion 524. As described above, in the illustrated embodiment, each of the plurality of electrode sites 522 wrap around an exterior of the sheath body 514 to form a ring electrode.

Figure 10A:
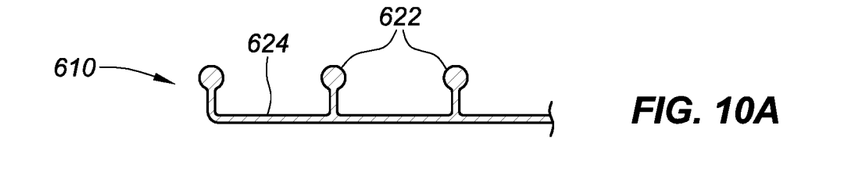
FIGS. 10A and 10B are isometric views of another embodiment of a medical device comprising a tracing support.
Figure 10B:
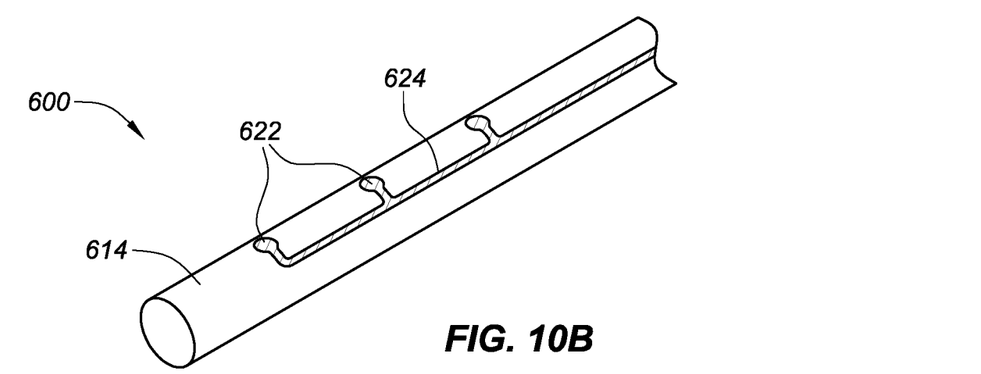

FIG. 10A depicts an isometric view of another embodiment of a tracing support 610 as described herein. The tracing support 610 can comprise a plurality of electrode sites 622 a conductor portion 624, As described herein, the tracing support can comprise a flexible material. The tracing support 610 can be rolled and reflowed around a sheath as described herein. In the illustrated embodiment, each of the plurality of electrode sites 622 are disposed on the same side of a longitudinal axis 620 of the tracing support 610. By placing the plurality of electrode sites on the same side of the longitudinal axis, each of the electrode sites can form a continuous line of electrodes when rolled and reflowed onto a sheath. In other embodiments, the plurality of electrode sites can be placed in different configurations. In one embodiment, the plurality of electrode sites can alternate sides of the longitudinal axis of the tracing support. In another embodiment, one of the plurality of electrodes can be placed on an opposite side of the longitudinal axis. In yet another embodiment, each of the plurality of electrode sites can be disposed on the same side of the longitudinal axis, but comprise various lengths of conductor portions coupling each of the electrode sites to the main portion of the conductor portion. As a result, the placement of each of the plurality of electrode sites can be varied and determined before final manufacturing. FIG. 10B depicts an isometric view of the tracing support of FIG. 10A after it has been rolled and reflowed onto a sheath. The sheath 600 can comprise a sheath body 614 and a tracing support 610. The tracing support can comprise a plurality of electrode sites 622 and a conductor portion 624. As described above, each of the plurality of electrode sites can be disposed along a continuous line or plane of the sheath.

While the above description focuses on describing deflectable sheaths, the components described herein can also be utilized in fixed curve introducers, fixed curve catheters, deflectable catheters, and other medical devices. These devices can comprise at least one electrode. In some embodiments, these devices can comprise ten electrodes, twenty electrodes, or more used for diagnostic or therapeutic purposes.

Further, although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

What is claimed is:

1. A medical device comprising:
    a sheath body comprising:
        a first layer;
        a second layer;
        a third layer, wherein the second layer is disposed between the first layer and the third layer;
        a braided wire assembly that is encased within the second layer;
        a tracing support that is encased within the second layer, wherein the tracing support comprises a base layer, electrode tabs, and conductor traces, wherein each of the electrode tabs forms an electrode, wherein the conductor traces are disposed between the braided wire assembly and an outer surface of the second layer, wherein the electrode tabs and the conductor traces are formed by adding an electrically conductive material to the base layer via an electrical tracing process, a photo etching process, or an additive manufacturing process so that each of the conductor traces is connected to a respective one of the electrode tabs;
        a central major lumen extending through the sheath body along a longitudinal axis, wherein the central major lumen is defined by the first layer;
        at least one outer lumen extending through the sheath body, wherein the at least one outer lumen is disposed within the second layer; and
        at least one deflection element extending through the sheath body; and
    an actuator coupled to a proximal end of the sheath body, wherein the actuator is further coupled to the at least one deflection element and capable of deflecting a distal end of the sheath body.

2. The medical device according to claim 1, wherein the braided wire assembly comprises a rectangular cross-section.

3. The medical device according to claim 1, further comprising a minor hollow tube encased within the second layer and defining the outer lumen.

4. The medical device according to claim 1, wherein at least one of the conductor traces is disposed on a neutral axis of the sheath body.

5. The medical device according to claim 1, wherein the electrodes are configured as spot electrodes.

6. The medical device according to claim 1, wherein the electrodes are configured as ring electrodes.

7. The medical device according to claim 1, wherein the electrodes comprise materials different from the electrically conductive material.

8. The medical device according to claim 1, wherein the sheath body comprises a liquid crystal polymer.

9. The medical device according to claim 1, wherein the tracing support is rolled and reflowed on the outer surface of the second layer.

10. The medical device according to claim 1, wherein the base layer of the tracing support constitutes a sub-layer of the second layer that is coupled to an exterior portion of the braided wire assembly.

11. The medical device according to claim 1, wherein the second layer and the base layer comprise a reflowable material.

* * * * *